US012569176B2

(12) United States Patent (10) Patent No.: US 12,569,176 B2
Pratt (45) Date of Patent: Mar. 10, 2026

(54) VIRTUAL BLOCK TEST DESIGN FOR PSYCHOLOGY TESTING AND METHOD OF USE THEREOF

(71) Applicant: Jill E. Pratt, Mount Holly, NC (US)

(72) Inventor: Jill E. Pratt, Mount Holly, NC (US)

( * ) Notice: Subject to any disclaimer, the term of this patent is extended or adjusted under 35 U.S.C. 154(b) by 449 days.

(21) Appl. No.: 18/305,492

(22) Filed: Apr. 24, 2023

(65) Prior Publication Data

US 2024/0032831 A1 Feb. 1, 2024

Related U.S. Application Data

(60) Provisional application No. 63/392,965, filed on Jul. 28, 2022.

(51) Int. Cl.
*A61B 5/16* (2006.01)
*G06T 19/20* (2011.01)
(52) U.S. Cl.
CPC ................ *A61B 5/16* (2013.01); *G06T 19/20* (2013.01); *G06T 2219/2004* (2013.01); *G06T 2219/2016* (2013.01)
(58) Field of Classification Search
CPC .................................. A61B 5/16; G06T 19/20
See application file for complete search history.

(56) References Cited

U.S. PATENT DOCUMENTS 9,160,672 B2 * 10/2015 Short .................. H04L 61/4511
2007/0262984 A1 * 11/2007 Pruss ...................... G06T 19/20
345/420
2021/0337004 A1 * 10/2021 Shaffer .............. H04L 65/1073

OTHER PUBLICATIONS

Avery Dunn et al., "Measuring More to Learn More From the Block Design Test: A Literature Review", Proceedings of the 43rd Annual Meeting of the Cognitive Science Society, 2021. Dunn et al 2021—Measuring more to learn more from the block design test.pdf (Year: 2021).*

* cited by examiner

*Primary Examiner* — Yingchuan Zhang
(74) *Attorney, Agent, or Firm* — Jeffrey C. Watson, Esq.; Grell & Watson Patent Attorneys LLC

(57) ABSTRACT

A virtual block test design for psychology testing includes a computer system with a processor, a memory, a client input device, and a client display screen. The memory is configured to store a plurality of virtual block tests via the processor. The client display screen is configured to display a specified virtual block test from the plurality of virtual block tests via the processor. The client input device is configured to manipulate the specified virtual block test displayed on the client display screen via the processor. Wherein, the computer system is configured to allow a client to take the specified virtual block test displayed on the client display screen by utilizing the client input device to manipulate the specified virtual block test.

10 Claims, 9 Drawing Sheets practitioner                    client

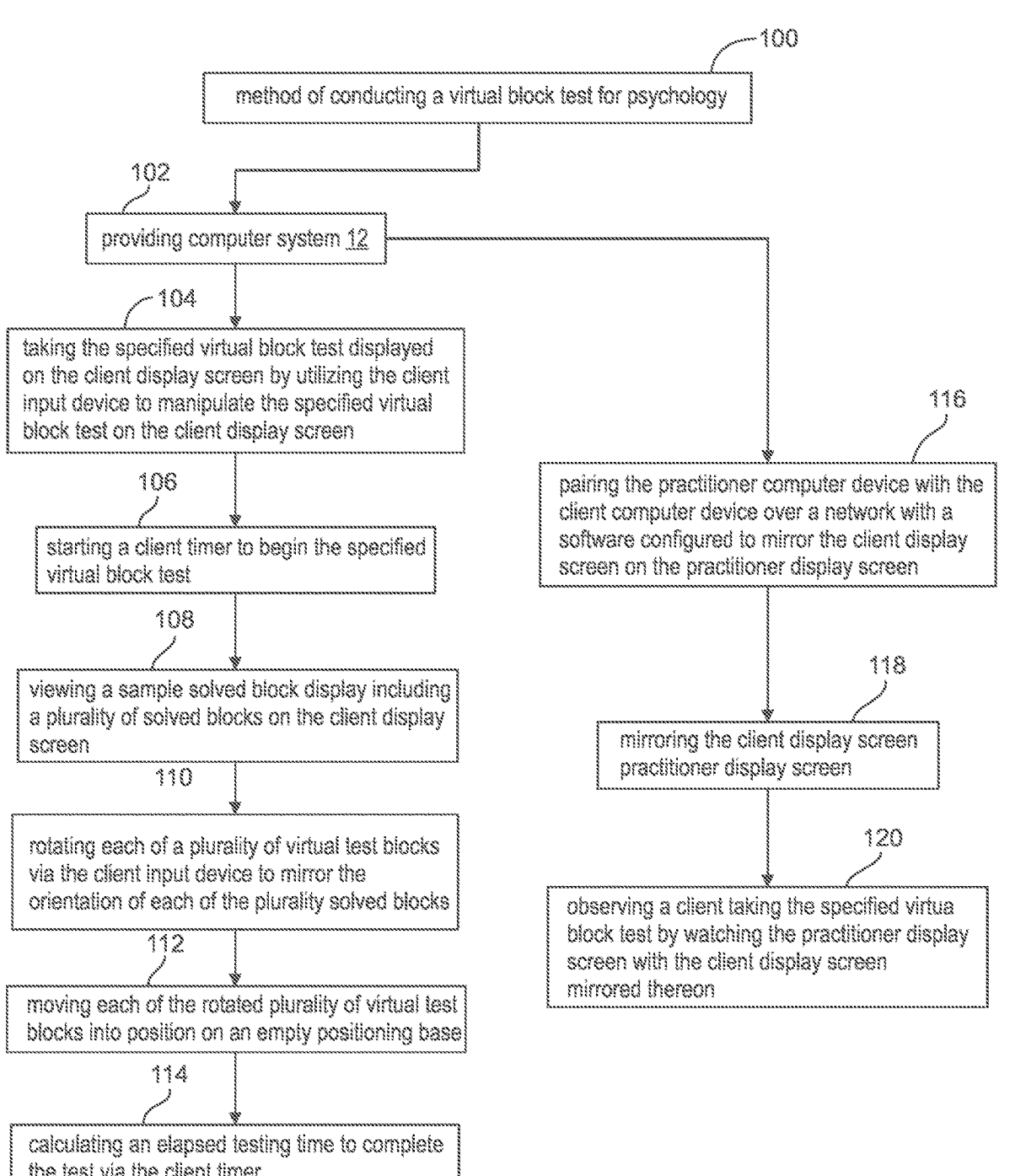

100 method of conducting a virtual block test for psychology

102 providing computer system 12

104 taking the specified virtual block test displayed on the client display screen by utilizing the client input device to manipulate the specified virtual block test on the client display screen

106 starting a client timer to begin the specified virtual block test

108 viewing a sample solved block display including a plurality of solved blocks on the client display screen

110 rotating each of a plurality of virtual test blocks via the client input device to mirror the orientation of each of the plurality solved blocks

112 moving each of the rotated plurality of virtual test blocks into position on an empty positioning base

114 calculating an elapsed testing time to complete the test via the client timer

116 pairing the practitioner computer device with the client computer device over a network with a software configured to mirror the client display screen on the practitioner display screen

118 mirroring the client display screen practitioner display screen

120 observing a client taking the specified virtua block test by watching the practitioner display screen with the client display screen mirrored thereon

FIG. 9

VIRTUAL BLOCK TEST DESIGN FOR PSYCHOLOGY TESTING AND METHOD OF USE THEREOF

CROSS-REFERENCE TO RELATED APPLICATIONS

This application claims benefit to U.S. Provisional Patent Application No. 63/392,965 filed on Jul. 28, 2022, entitled "VIRTUAL BLOCK DESIGN FOR PSYCHOLOGY TESTING", which is incorporated by reference in its entirety.

FIELD OF THE DISCLOSURE

The present disclosure relates to psychology testing, like a block design test for psychology. More specifically, the present disclosure related to a virtual block test design for psychology testing.

BACKGROUND

Generally speaking, a block design test is a subtest on many IQ test batteries used as part of assessment of human intelligence. It is thought to tap spatial visualization ability and motor skill. The test-taker uses hand movements to rearrange physical blocks that have various color patterns on different sides to match a pattern. The items in a block design test can be scored both by accuracy in matching the pattern and by speed in completing each item.

David Wechsler adapted a block design subtest for his Wechsler-Bellevue test, the predecessor of his WAIS (Wechsler Adult Intelligence Scale), from the Kohs block design test developed in 1920 at Stanford University by Samuel Calmin Kohs. A later revision of the Kohs test incorporated the time taken to complete each item into the scoring of the test. Wechsler followed that practice in making both accuracy and speed factors in scoring the test.

Good performance on the block design test is indicative of appropriate functioning of the parietal and frontal lobes. Head injury, Alzheimer's disease, and stroke can severely reduce the performance of an individual on the block design test. Preliminary findings may provide additional evidence that suggests impairment in block design performance among schizophrenic and bipolar disorder patient populations. The block design test is also a relatively accurate measure of spatial ability and spatial visualization ability used in daily life. The block design test is considered one of the best measures of spatial ability, although it is subject to certain problems of administration, such as anxiety or over-cautious responding. It has also been observed that autistic individuals may have superior performance in the block design test. Research has demonstrated the differences in construction time in the performance of the block design task by individuals with and without autism spectrum disorder. It has been claimed that in an unsegmented version of the task, people with high functioning autism performed significantly faster than neurotypical individuals. Performance on the block design test has also been suggested as a predictive measure for performance in fields such as engineering and physics.

The purpose of the disclosed virtual block test design for psychology testing may be to update the Wechsler subtest to be conducted solely online with a virtual format to align with the other Wechsler family of subtests that are already presented on a computer, tablet, IPad, the like, etc. Currently this subtest is administer using a set of physical Koh blocks that a student manipulates and touches 2D right in front of them. The pandemic forced the use of screen mirroring to watch the student do this activity with a trained adult monitor in their room. The test was not normed this way affecting the accuracy and validity of the results/scores. Thus, a disclaimer has had to be included in each psychological report documenting this change.

The instant disclosure may be designed to address at least certain aspects of the problems or needs discussed above by providing a virtual block test design for psychology testing.

SUMMARY

The present disclosure may solve the aforementioned limitations of the currently available block design tests for psychology, by providing a virtual block test design for psychology testing. The virtual block test design for psychology testing may generally include a computer system with a processor, a memory, a client input device, and a client display screen. The memory may be configured to store a plurality of virtual block tests via the processor. The client display screen may be configured to display a specified virtual block test from the plurality of virtual block tests via the processor. The client input device may be configured to manipulate the specified virtual block test displayed on the client display screen via the processor. Wherein, the computer system may be configured to allow a client to take the specified virtual block test displayed on the client display screen by utilizing the client input device to manipulate the specified virtual block test.

In select embodiments of the disclosed virtual block test design for psychology testing, the specified virtual block test displayed on the client display screen may include a sample solved block display and a plurality of virtual test blocks. The sample solved block display may include a plurality of solved blocks. The plurality of virtual test blocks may be configured to be manipulated by the client via the client input device. The plurality of virtual test blocks may include a same number of blocks as the plurality of solved blocks from the sample solved block display. Each of the plurality of virtual test blocks may include a same pattern to mirror one of the plurality of solved blocks from the sample solved block display. Wherein, the computer system may be configured to allow the client to take the specified virtual block test displayed on the client display screen by utilizing the client input device to manipulate each of the plurality of virtual test blocks to orient and position each of the plurality of virtual test blocks to mirror the sample solved block display.

One feature of the disclosed virtual block test design for psychology testing may be that the specified virtual block test displayed on the client display screen may include an empty positioning base. The empty positioning base may be sized and oriented to mirror a bottom of the sample solved block display. Wherein, the computer system may be configured to allow the client to take the specified virtual block test displayed on the client display screen by utilizing the client input device to manipulate each of the plurality of virtual test blocks to orient and position each of the plurality of virtual test blocks on the empty positioning base to mirror the sample solved block display.

Another feature of the disclosed virtual block test design for psychology testing may be that the client input device may be configured to rotate each of the plurality of virtual test blocks and to move each of the plurality of virtual test blocks.

In select embodiments of the disclosed virtual block test design for psychology testing, the same number of blocks of the sample solved block display and the plurality of virtual test blocks may include, but is not limited to: two blocks; four blocks; and nine blocks.

Another feature of the disclosed virtual block test design for psychology testing may be that each of the plurality of virtual test blocks may be a three-dimensional virtual cube. In select embodiments, each of the three-dimensional virtual cubes may be configured to rotate and move between red faces, white faces, and red-white right triangle faces. However, the disclosure is not so limited, and the virtual test blocks may be any virtual shapes, including, but not limited to, any 2-dimensional test shapes, and/or any 3-dimensional test shapes, like square pyramids, cubes, dodecahedron, icosahedron, octahedron, the like, etc. In addition, the virtual test blocks may include any desired patterns, sizes, color schemes, the like, etc. to mimic any standardized psychology tests, or to create new psychology testing or the like.

In select embodiments of the disclosed virtual block test design for psychology testing, the client input device may be a mouse, a keyboard, a touch screen, a stylus pen, the like, and/or combinations thereof. Wherein the computer system may be configured to allow the client to take the specified virtual block test displayed on the client display screen by utilizing the mouse, the keyboard, the touch screen, the stylus pen, the like, and/or the combinations thereof to manipulate the specified virtual block test.

Another feature of the disclosed virtual block test design for psychology testing may be that the computer system may further include a client timer. The client timer may be configured to time the client while taking the specified virtual block test. Wherein, the client display screen may be configured to display an elapsed testing time from the client timer via the processor. In select embodiments, the client display screen may include a start button. The start button may be positioned with the elapsed testing time. The start button may be configured to activate the specified virtual block test. Wherein, when the client is ready to begin the specified virtual block test, the start button may be configured to be pressed with the client input device, whereby the client timer starts counting and displaying the elapsed testing time until the specified virtual block test is completed.

In select embodiments of the disclosed virtual block test design for psychology testing, the specified virtual block test may be manually selected from the plurality of virtual block tests.

In other select embodiments of the disclosed virtual block test design for psychology testing, the specified virtual block test may be randomly assigned from the plurality of virtual block tests via the processor.

In select embodiments of the disclosed virtual block test design for psychology testing, the computer system may include a client computer device. The client computer device may include the client display screen and the client input device. The client computer device may be a tablet, a personal computer, a desktop computer, a laptop, a mobile device, other computer devices, or the like.

In select embodiments of the disclosed virtual block test design for psychology testing, the computer system may include a practitioner computer device. The practitioner computer device may have a practitioner display screen. The practitioner computer device may be in communication with the client display screen over a network. Wherein, the practitioner display screen may be configured to mirror the client display screen on the practitioner computer device. Whereby, the practitioner computer device may be configured to allow a practitioner to monitor the client taking the specified virtual block test via the practitioner display screen. In select embodiments, the practitioner computer device may be a tablet, a personal computer, a desktop computer, a laptop, a mobile device, other computer devices, or the like.

In select embodiments of the disclosed virtual block test design for psychology testing, the practitioner computer device and the client computer device may be paired via an interactive testing software program.

Another feature of the disclosed virtual block test design for psychology testing may be that it is designed and configured to update a Wechsler subtest to be conducted solely online with a virtual format. However, the disclosure is not so limited, and other cognitive tests with colored or physical objects may also become virtual utilizing the disclosed design for psychology testing.

In another aspect, the instant disclosure embraces the virtual block test design for psychology testing in any embodiment and/or combination of embodiments shown and/or described herein.

In another aspect, the instant disclosure embraces a method of conducting a virtual block test for psychology. The disclosed method of conducting a virtual block test for psychology may generally include utilizing the disclosed virtual block test design for psychology testing in any embodiment and/or combination of embodiments shown and/or described herein. As such, the disclosed method of conducting a virtual block test for psychology may generally include providing the disclosed computer system in any embodiment and/or combination of embodiments shown and/or described herein. The provided computer system may generally have a processor, a memory, a client input device, and a client display screen. The memory may be configured to store a plurality of virtual block tests via the processor. The client display screen may be configured to display a specified virtual block test from the plurality of virtual block tests via the processor. The client input device may be configured to manipulate the specified virtual block test displayed on the client display screen via the processor. With the provided computer system, the method of conducting a virtual block test for psychology may further include taking the specified virtual block test displayed on the client display screen by utilizing the client input device to manipulate the specified virtual block test on the client display screen.

In select embodiments of the disclosed method of conducting a virtual block test for psychology, the step of taking the specified virtual block test displayed on the client display screen by utilizing the client input device to manipulate the specified virtual block test on the client display screen may include: starting a client timer to begin the specified virtual block test; viewing a sample solved block display including a plurality of solved blocks on the client display screen; rotating each of a plurality of virtual test blocks via the client input device to mirror the orientation of each of the plurality of solved blocks; moving each of the rotated plurality of virtual test blocks into position on an empty positioning base; and calculating an elapsed testing time to complete the test via the client timer.

In select embodiments of the disclosed method of conducting a virtual block test for psychology, wherein the provided computer system further including a practitioner computer device with a practitioner display screen, the disclosed method of conducting a virtual block test for psychology may further include: pairing the practitioner computer device with the client computer device over a network with a software configured to mirror the client display screen on the practitioner display screen; mirroring the client display screen on the practitioner display screen;

and observing a client taking the specified virtual block test by watching the practitioner display screen with the client display screen mirrored thereon.

The foregoing illustrative summary, as well as other exemplary objectives and/or advantages of the disclosure, and the manner in which the same are accomplished, are further explained within the following detailed description and its accompanying drawings.

BRIEF DESCRIPTION OF THE DRAWINGS

The present disclosure will be better understood by reading the Detailed Description with reference to the accompanying drawings, which are not necessarily drawn to scale, and in which like reference numerals denote similar structure and refer to like elements throughout, and in which:

FIG. 9 is a flow chart of a meth of conducting a virtual block psychology test according to select embodiments of the instant disclosure.

Figure 1:
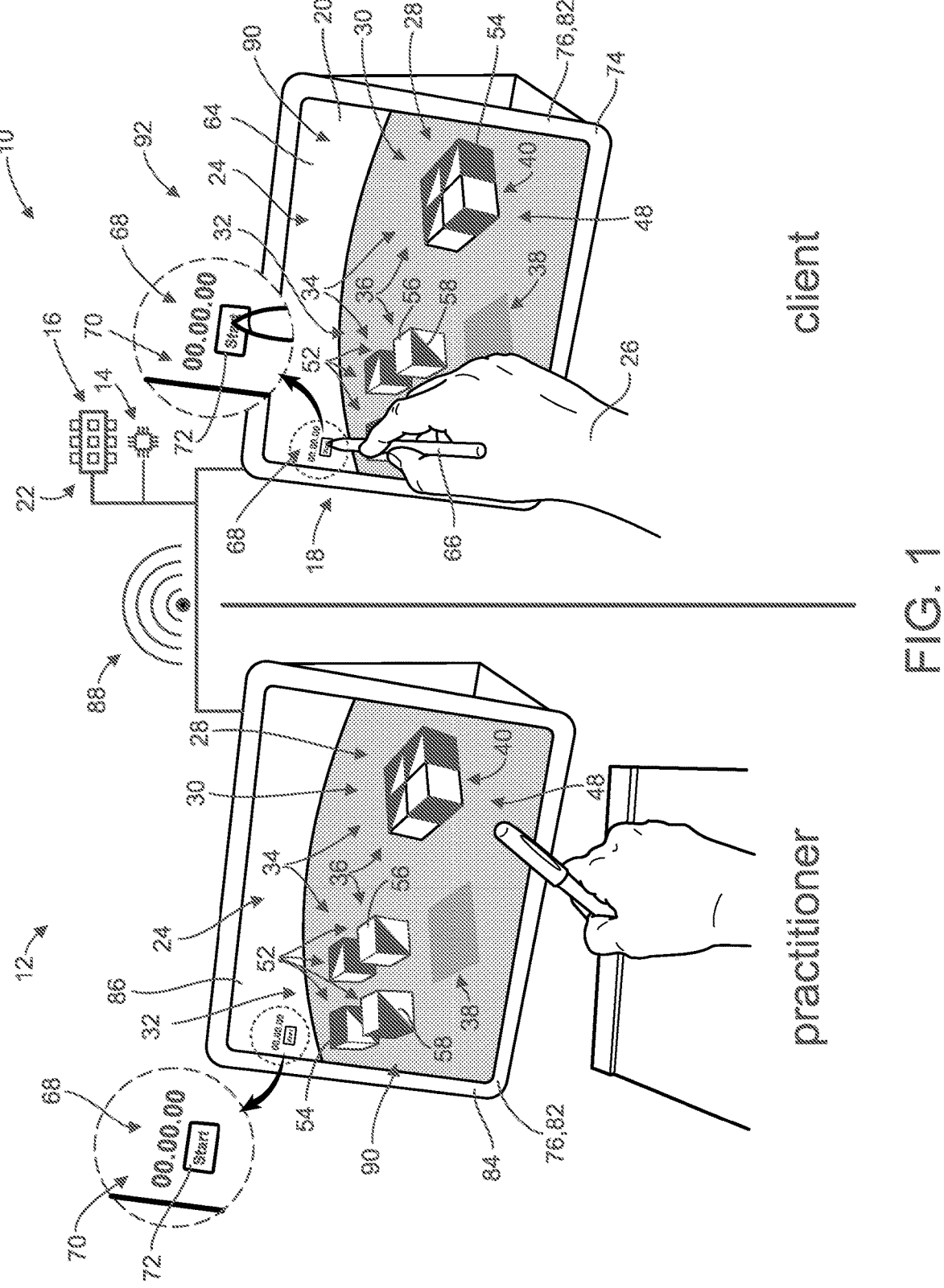
FIG. 1 is a perspective split environmental view of the virtual block test design for psychology testing according to select embodiments of the instant disclosure, showing the practitioner setup and the client setup.
Figure 2:
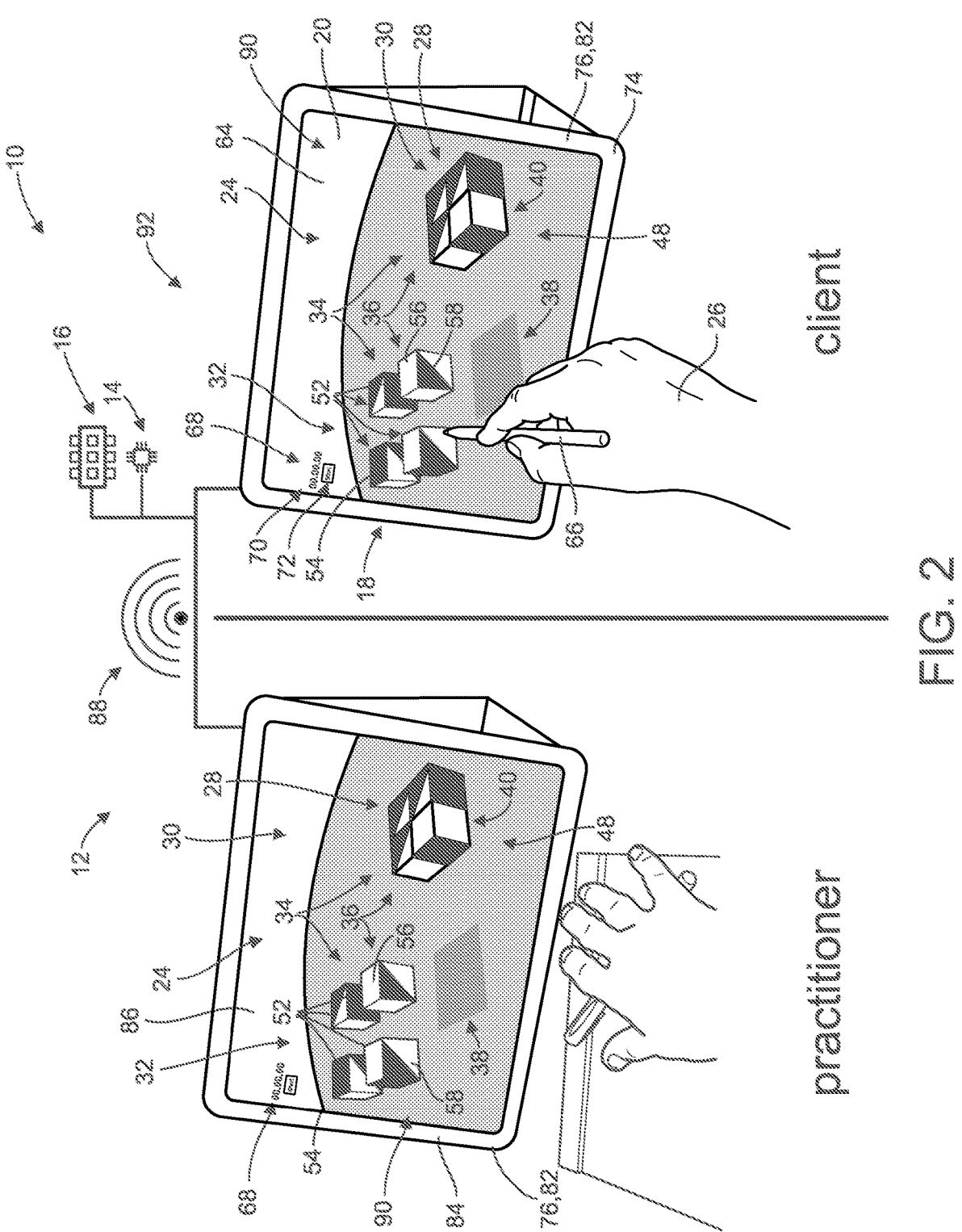
FIG. 2 is another perspective split environmental view of the virtual block test design for psychology testing of FIG. 1, showing the practitioner setup ready to observe and the client setup ready to begin the test.

It is to be noted that the drawings presented are intended solely for the purpose of illustration and that they are, therefore, neither desired nor intended to limit the disclosure to any or all of the exact details of construction shown, except insofar as they may be deemed essential to the claimed disclosure.

DETAILED DESCRIPTION

Referring now to FIGS. 1-9, in describing the exemplary embodiments of the present disclosure, specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples and are merely examples among other possible examples.

Referring to FIGS. 1-8, the present disclosure may solve the aforementioned limitations of the currently available block design tests for psychology, by providing virtual block test design 10 for psychology testing. Virtual block test design 10 for psychology testing may generally include computer system 12. Computer system 12 may include any type of computer system and may generally include processor 14, memory 16, client input device 18, and client display screen 20. Memory 16 may be configured to store a plurality of virtual block tests 22 via processor 14. Client display screen 20 may be configured to display specified virtual block test 24 from the plurality of virtual block tests 22 via processor 14. Client input device 18 may be configured to manipulate the specified virtual block test 24 displayed on the client display screen 20 via processor 14. Wherein, computer system 12 may be configured to allow client 26 to take specified virtual block test 24 displayed on client display screen 20 by utilizing client input device 18 to manipulate specified virtual block test 24.

As shown in FIGS. 1-8, in select embodiments of virtual block test design 10 for psychology testing, specified virtual block test 24 displayed on client display screen 20 may include sample solved block display 28 and a plurality of virtual test blocks 32. The sample solved block display 28 may include a plurality of solved blocks 30 put together in the position and orientation required to solve specified virtual block test 24. The plurality of virtual test blocks 32 may be configured to be manipulated by client 26 via client input device 18. The plurality of virtual test blocks 32 may include same number of blocks 34 as the plurality of solved blocks 30 from the sample solved block display 28. Each of the plurality of virtual test blocks 32 may also include same pattern 36 to mirror one of the plurality of solved blocks 30 from the sample solved block display 28. Wherein, computer system 12 may be configured to allow client 26 to take the specified virtual block test 24 displayed on client display screen 20 by utilizing client input device 18 to manipulate each of the plurality of virtual test blocks 32 to orient and position each of the plurality of virtual test blocks 32 to mirror the sample solved block display 28.

Still referring to FIGS. 1-8, one feature of the disclosed virtual block test design 10 for psychology testing may be that the specified virtual block test 24 displayed on the client display screen 20 may include empty positioning base 38. Empty positioning base 38 may be for providing a virtual space or virtual frame for client 26 to position and orient the plurality of virtual test blocks 32 to match sample solved block display 28. As such, empty positioning base 38 may be sized and oriented to mirror bottom 40 of sample solved block display 28. Wherein, computer system 12 may be configured to allow client 26 to take specified virtual block test 24 displayed on client display screen 20 by utilizing client input device 18 to manipulate each of the plurality of virtual test blocks 32 to orient and position each of the plurality of virtual test blocks 32 on empty positioning base 38 to mirror the sample solved block display 28.

Figure 3:
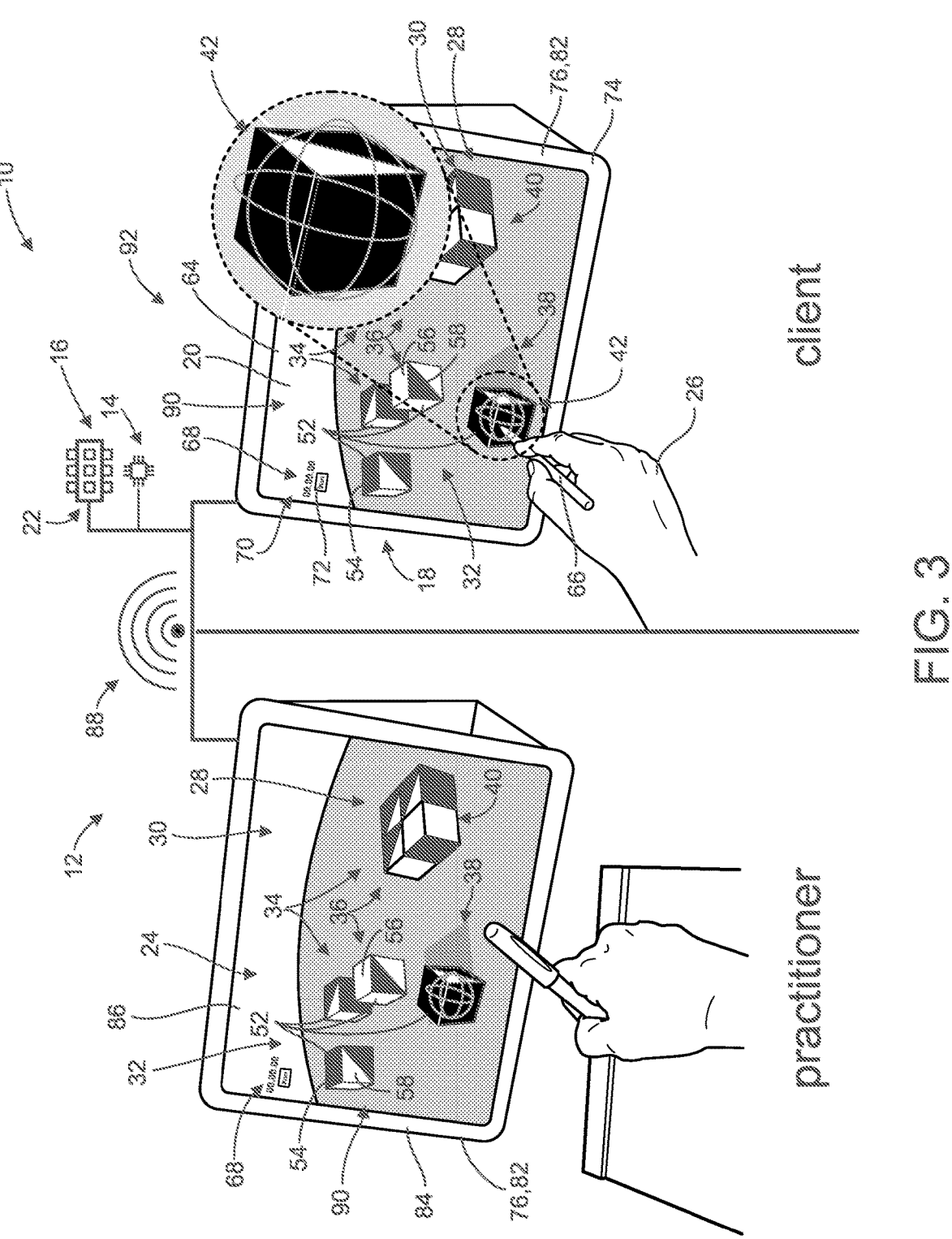
FIG. 3 is another perspective split environmental view of the virtual block test design for psychology testing of FIG. 1, showing the practitioner observing the client and the client testing utilizing a pen or stylus to manipulate the blocks on the screen.
Figure 4:
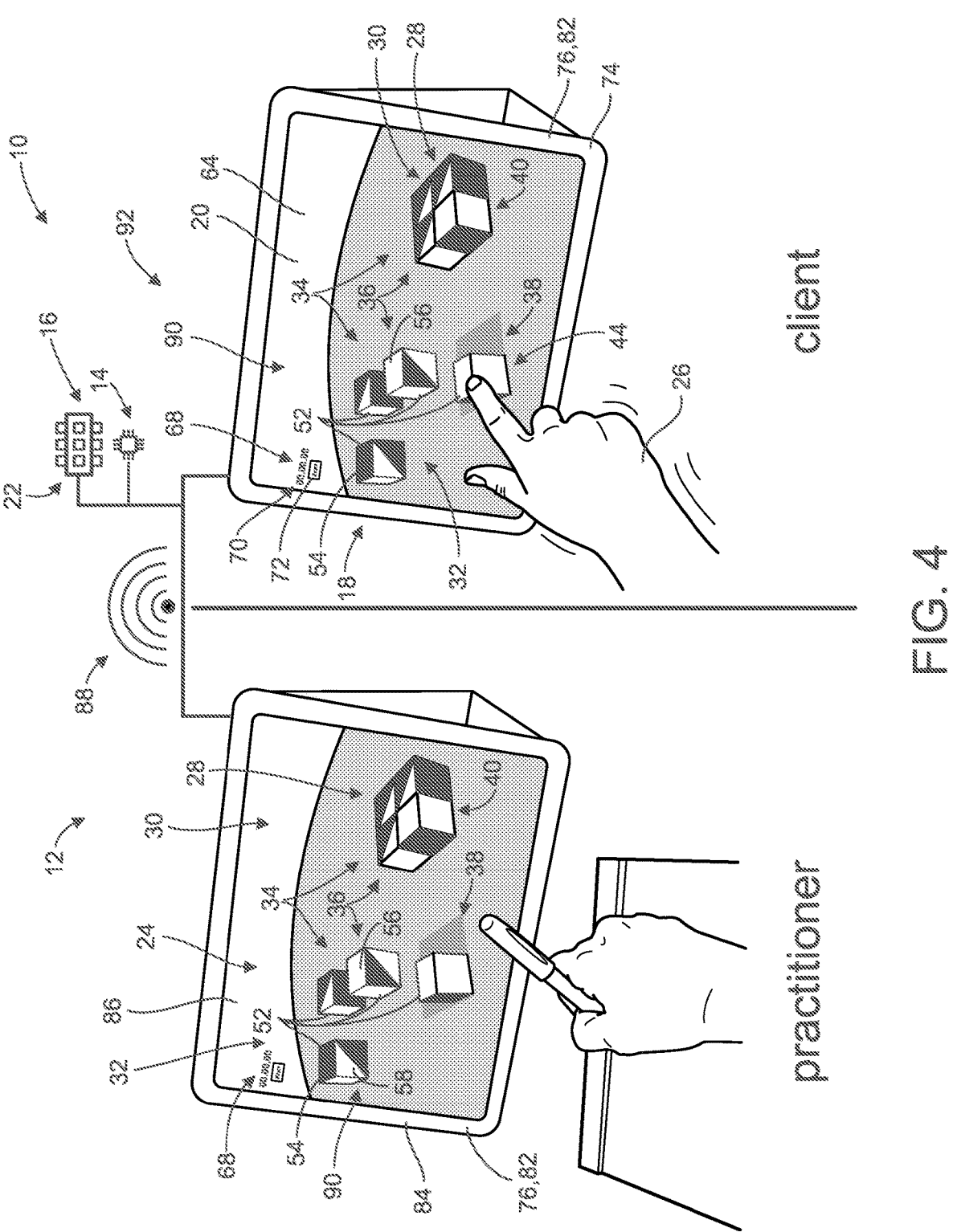
FIG. 4 is another perspective split environmental view of the virtual block test design for psychology testing of FIG. 1, showing the practitioner observing the client and the client testing using a finger to manipulate the blocks on the screen.
Figure 5:
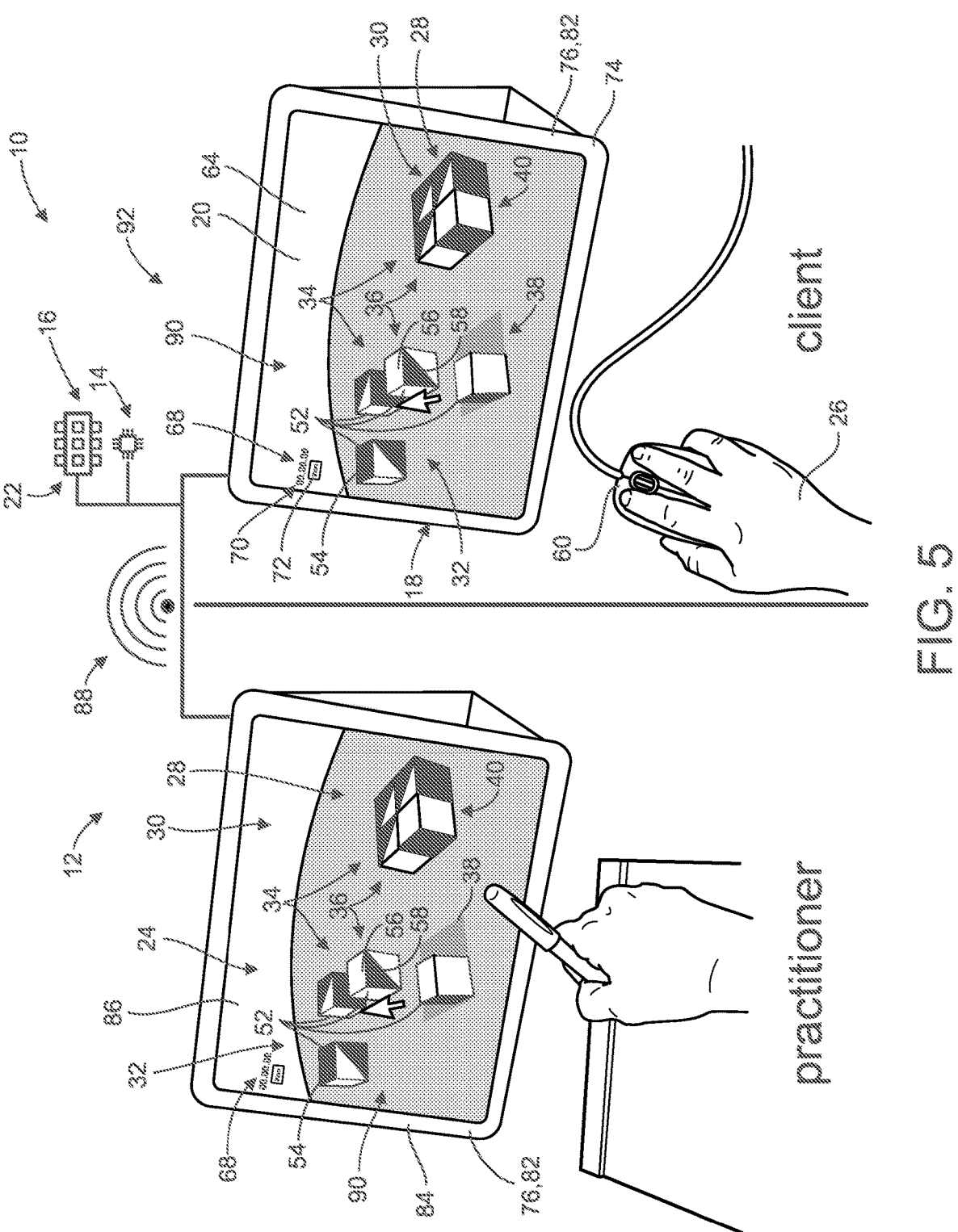
FIG. 5 is another perspective split environmental view of the virtual block test design for psychology testing of FIG. 1, showing the practitioner observing the client and the client testing using a mouse to manipulate the blocks on the screen.
Figure 6:
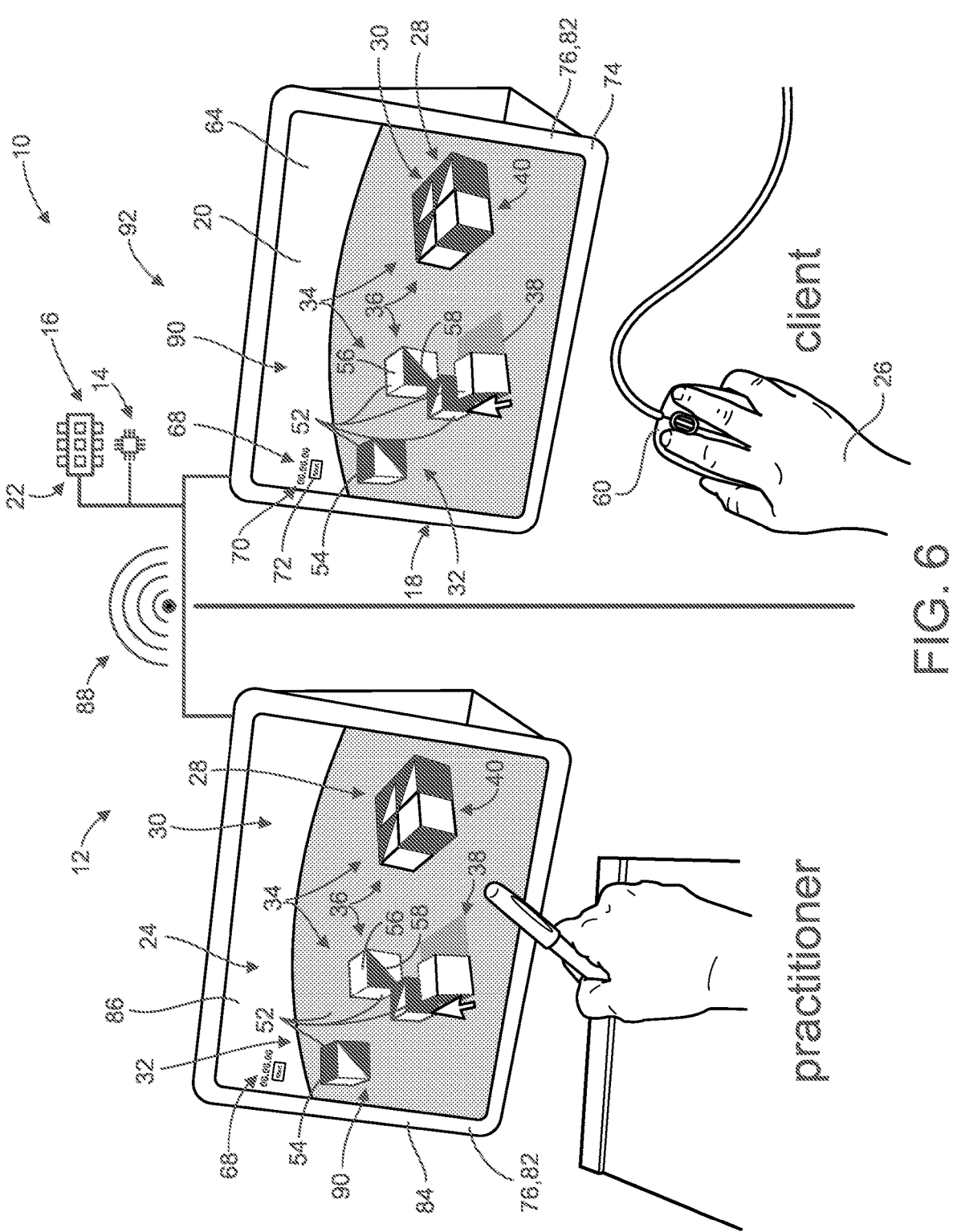
FIG. 6 is another perspective split environmental view of the virtual block test design for psychology testing of FIG. 1, showing the practitioner observing the client and the client testing using a mouse to manipulate the blocks on the screen.
Figure 7:
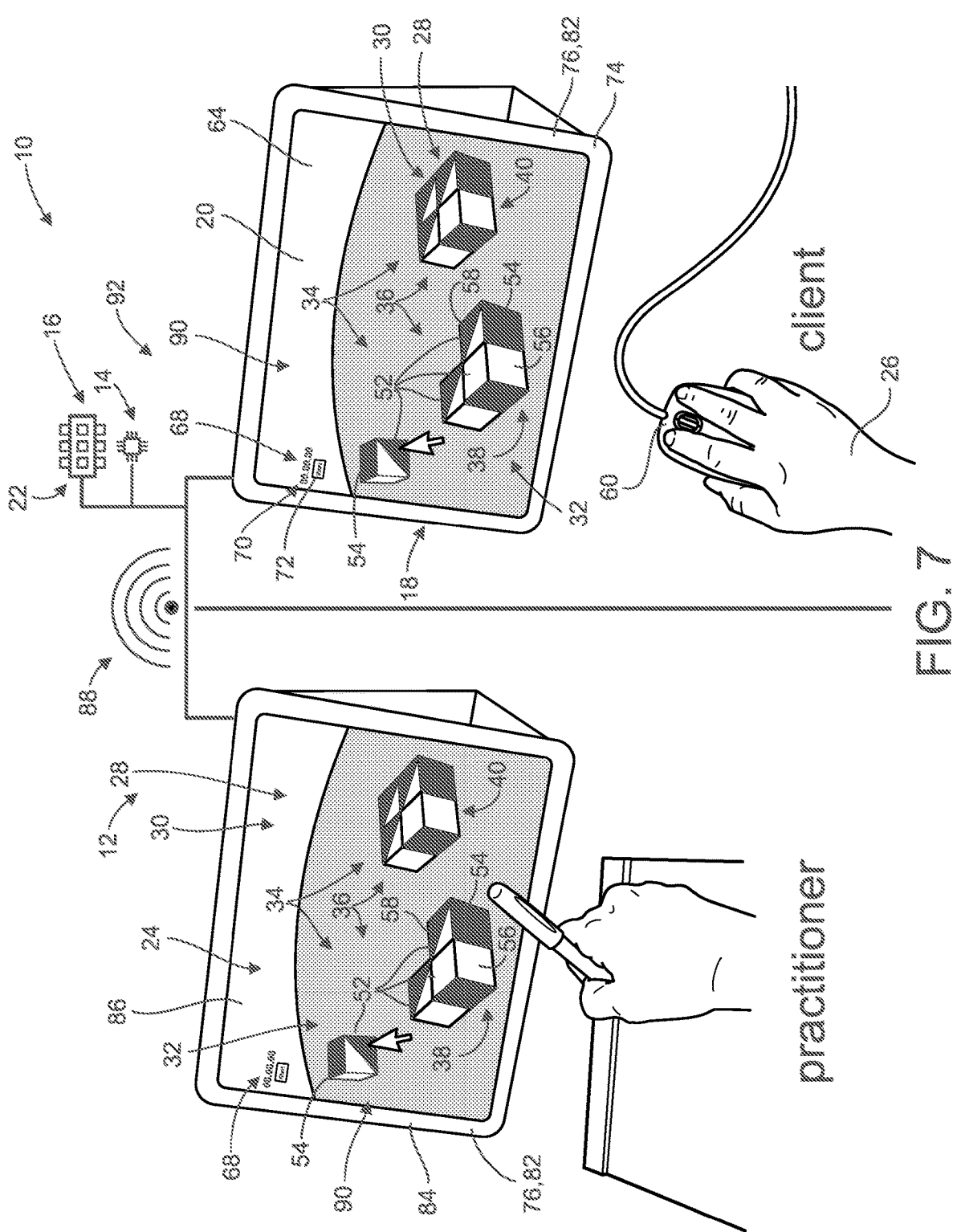
FIG. 7 is another perspective split environmental view of the virtual block test design for psychology testing of FIG. 1, showing the practitioner observing the client and the client testing using a mouse to manipulate the blocks on the screen.

Referring now specifically to FIGS. 3 and 4, another feature of virtual block test design 10 for psychology testing may be that client input device 18 may be configured to rotate 42 each of the plurality of virtual test blocks 32 (FIG. 3) and to move 44 (FIG. 4) each of the plurality of virtual test blocks 32.

Still referring to FIGS. 1-8, virtual block test design 10 for psychology testing may include any various size, number, patterns, and/or orientation of specified virtual block test 24. In select embodiments of virtual block test design 10 for psychology testing, same number 34 of blocks of sample solved block display 28 and plurality of virtual test blocks 32 may include, but is not limited to: two blocks; four blocks (as shown in the Figures); and nine blocks.

Still referring to FIGS. 1-8, another feature of virtual block test design 10 for psychology testing may be that each of the plurality of virtual test blocks 32 may be three-dimensional virtual cube 52. Each of the three-dimensional virtual cubes 52 may be configured to rotate (see FIG. 3) and move (see FIG. 4) between various faces of each three-dimensional virtual cube, including, but not limited to, red faces 54, white faces 56, and red-white right triangle faces 58, as currently known as Koh blocks used in the physical world for certain Wechsler subtests. However, the disclosure is not so limited, and the virtual test blocks 32 may be any virtual shapes, including, but not limited to, any 2-dimensional test shapes, and/or any 3-dimensional test shapes, like square pyramids, cubes, dodecahedron, icosahedron, octahedron, the like, etc. In addition, the virtual test blocks 32 may include any desired patterns, sizes, color schemes, the like, etc. to mimic any standardized psychology tests, or to create new psychology testing or the like.

Still referring to FIGS. 1-8, client input device 18 of computer system 12 used for virtual block test design 10 for psychology testing may include any form of computer input devices for manipulating the plurality of virtual test blocks on client display screen 20. In select embodiments of virtual block test design 10 for psychology testing, client input device 18 may be mouse 60 (see FIGS. 5, 6 and 7), a keyboard, touch screen 64 (see FIGS. 1-8), stylus pen 66 (see FIGS. 1-3), the like, and/or combinations thereof. Wherein, computer system 12 may be configured to allow client 26 to take the specified virtual block test 24 displayed on client display screen 20 by utilizing mouse 60, the keyboard, touch screen 64, stylus pen 66, the like, and/or combinations thereof to manipulate specified virtual block test 24.

Figure 8:
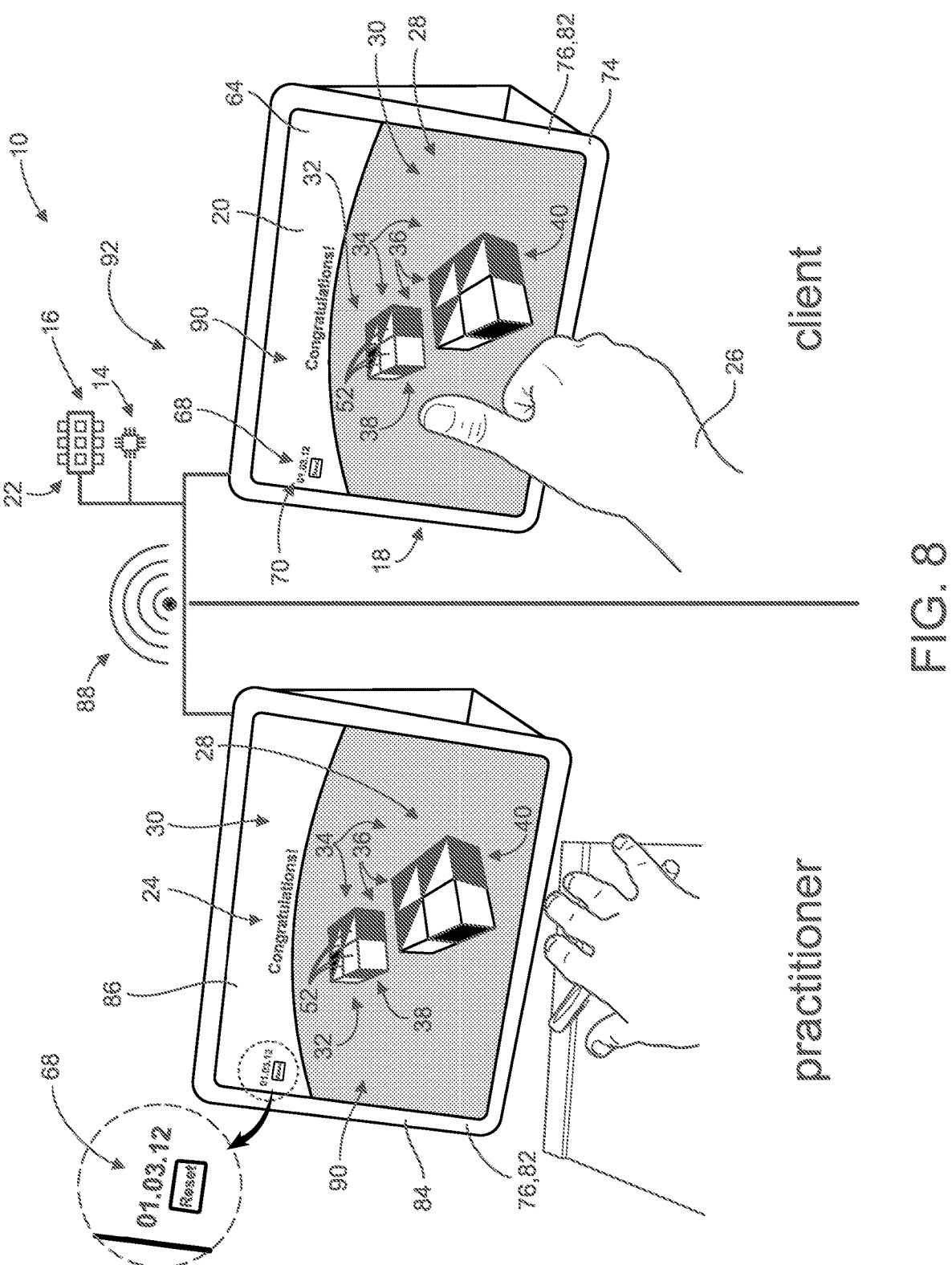
FIG. 8 is another perspective split environmental view of the virtual block test design for psychology testing of FIG. 1, showing the practitioner observing the client and the client completing the test.

Still referring to FIGS. 1-8, another feature of virtual block test design 10 for psychology testing may be that computer system 12 may further include client timer 68. Client timer 68 may be configured to time client 26 while taking the specified virtual block test 24. Wherein, client display screen 20 may be configured to display elapsed testing time 70 from client timer 68 via processor 14. In select embodiments, client display screen 20 may include start button 72. Start button 72 may be positioned with elapsed testing time 70. Start button 72 may be configured to activate the specified virtual block test 24. Wherein, when client 26 is ready to begin the specified virtual block test 24, start button 72 may be configured to be pressed with client input device 18, whereby client timer 68 starts counting and displaying elapsed testing time 70 until the specified virtual block test 24 is completed. As shown in FIG. 8, once the specified virtual block test 24 is completed, a reset button may be presented for resetting client timer 68 and starting a new specified virtual block test 24 from the plurality of virtual block tests 22 stored in memory 16 of computer system 12. In select embodiments of virtual block test design 10 for psychology testing, the new specified virtual block test 24 may be manually selected from the plurality of virtual block tests 22. In other select embodiments of virtual block test design 10 for psychology testing, the new specified virtual block test 24 may be randomly assigned from the plurality of virtual block tests 22 via processor 14.

Still referring to FIGS. 1-8, in select embodiments of virtual block test design 10 for psychology testing, computer system 12 may include client computer device 74. Client computer device 74 may generally include client display screen 20 and client input device 18. Client computer device 74 may be any type of computer device or machine configured to include client display screen 20 and client input device 18 for taking specified virtual block test 24 on such computer device or machine. In select embodiments of virtual block test design 10 for psychology testing, client computer device 74 may be tablet 76 (as shown in the Figures), a personal computer, a desktop computer, a laptop, mobile device 82 (as shown in the Figures), other computer devices, or the like.

Still referring to FIGS. 1-8, in select embodiments of virtual block test design 10 for psychology testing, computer system 12 may include practitioner computer device 84. Practitioner computer device 84 may be designed and configured for allowing a practitioner to virtually observe, monitor, and or administer virtual block test design 10 to client 26. Practitioner computer device 84 may generally include practitioner display screen 86. Practitioner computer device 84 may be in communication with client display screen 20 on client computer device 74 over network 88. Network 88 may be any wired or wireless communication network, including, but not limited to, an ethernet network, an internet network, a Wi-Fi connection, a shortrange wireless technology standard (e.g. Bluetooth®) connection, the like, and/or combinations thereof. Wherein, practitioner display screen 86 may be configured to mirror client display screen 20 on practitioner computer device 84. Whereby, practitioner computer device 84 may be configured to allow a practitioner to monitor client 26 taking specified virtual block test 24 via practitioner display screen 86. Practitioner computer device 84 may be any type of computer device or machine configured to include practitioner display screen 86 for observing client taking specified virtual block test 24 on such computer device or machine. In select embodiments of virtual block test design 10 for psychology testing, practitioner computer device 84 may be tablet 76 (as shown in the Figures), a personal computer, a desktop computer, a laptop, mobile device 82 (as shown in the Figures), other computer devices, or the like. In select embodiments of virtual block test design 10 for psychology testing, practitioner computer device 84 and client computer device 74 may be paired via interactive testing software program 90. Interactive testing software program 90 may be designed and configured to pair practitioner computer device 84 and client computer device 74 to allow the practitioner to virtually observe, monitor, and or administer virtual block test design 10 to client 26. In select embodiments, interactive testing software program 90 may be, or may be similar to, a Q-Interactive® software program, as provided by Pearson of San Antonio, Texas. However, the disclosure is not so limited, and other displays within Q-Global® (as provided by Pearson of San Antonio, Texas) could be used, like where it could be used with those who are not subscribed to Q-Interactive®. As an example, the practitioner could put design 10 on Q-Global® (as provided by Pearson of San Antonio, Texas) for schools, or the like, that do not use Ipads. Another feature of virtual block test design 10 for psychology testing may be that it may be designed and configured to update a Wechsler subtest to be conducted solely online with virtual format 92. However, the disclosure is not so limited, and other cognitive tests with colored or physical objects may also become virtual utilizing the disclosed design 10 for psychology testing.

Referring now specifically to FIG. 9, in another aspect, the instant disclosure embraces method 100 of conducting a virtual block test for psychology. The disclosed method 100 of conducting a virtual block test for psychology may generally include utilizing the disclosed virtual block test design 10 for psychology testing in any embodiment and/or combination of embodiments shown and/or described herein. As such, the disclosed method 100 of conducting a virtual block test for psychology may generally include step 102 of providing the disclosed computer system 12 in any embodiment and/or combination of embodiments shown and/or described herein. The provided computer system 12 may generally have processor 14, memory 16, client input device 18, and client display screen 20. Memory 16 may be configured to store the plurality of virtual block tests 22 via processor 14. The client display screen 20 may be configured to display specified virtual block test 24 from the plurality of virtual block tests 22 via processor 14. The client input device 18 may be configured to manipulate the specified virtual block test 24 displayed on client display screen 20 via processor 14. With the provided computer system 12, method 100 of conducting a virtual block test for psychology may further include step 104 of taking the specified virtual block test 24 displayed on the client display screen 20 by utilizing the client input device 18 to manipulate the specified virtual block test 24 on the client display screen 20.

Still referring to FIG. 9, in select embodiments of the disclosed method 100 of conducting a virtual block test for psychology, step 104 of taking the specified virtual block test 24 displayed on the client display screen 20 by utilizing the client input device 18 to manipulate the specified virtual block test 24 on the client display screen 20 may include: step 106 of starting client timer 68 to begin the specified virtual block test 24; step 108 of viewing sample solved block display 28 including the plurality of solved blocks 30 on client display screen 20; step 110 of rotating each of a plurality of virtual test blocks 32 via the client input device 18 to mirror the orientation of each of the plurality of solved blocks 30; step 112 of moving each of the rotated plurality of virtual test blocks 32 into position on empty positioning base 38; and step 114 of calculating elapsed testing time 70 to complete the test via client timer 68.

Still referring to FIG. 9, in select embodiments of the disclosed method 100 of conducting a virtual block test for psychology, wherein the provided computer system 12 further including practitioner computer device 84 with practitioner display screen 86, the disclosed method 100 of conducting a virtual block test for psychology may further include: step 116 of pairing the practitioner computer device 84 with client computer device 74 over network 88 with interactive testing software 90 configured to mirror client display screen 20 on practitioner display screen 86; step 118 of mirroring client display screen 20 on practitioner display screen 86; and step 120 of observing client 26 taking the specified virtual block test 24 by watching the practitioner display screen 86 with the client display screen 20 mirrored thereon.

In sum, the purpose of the disclosed virtual block test design 10 for psychology testing may be to update the Wechsler subtest to be conducted solely online with virtual format 92 to align with the other Wechsler family of subtests that are already presented on a computer, tablet, iPad, the like, etc. Currently, this subtest is administer using a set of physical Koh blocks that a student manipulates and touches right in front of them. The pandemic forced the use of screen mirroring to watch the student do this activity with a trained adult monitor in their room. The test was not normed this way affecting the accuracy and validity of the results/scores. A disclaimer thus has had to be included in each psychological report documenting this change. Currently, equivalency studies are being used to confirm that the scores are similar, as a quick stop gap measure because of COVID. However, the digital version is supposed to be more efficient and cohesive. Right now, blocks are mailed to the examinee. The examiner thus needs a document camera and another (non-psychologist support person) with the examinee to ensure that the blocks are laid out properly which affects confidentiality and test item security. Thus, providing design 10 is ideal.

In use, with the disclosed virtual block test design 10 for psychology testing, a practitioner and client paired set of IPads (Pearson has most tests on Q-Interactive® Platform) may be used to administer virtual format 92 of block testing. On the practitioner display screen 86 may be a picture of the correct design and a stopwatch/timer to record elapsed testing time 70. On the client display screen 20 on the left side are 2, 4, or 9 blocks depending upon the design, the design at the top middle of the screen and an empty positioning base 38 for the client 26 to move and place the virtual test blocks 32 to make the correct testing design. Each item is presented on a new screen with the same layout for practitioner/client. The plurality of virtual test blocks are 3D and can rotate and move between red faces 54, white faces 56, and red/white (right triangles) faces 58 on a 3-D virtual cube 52, like as the Koh wooden blocks are made for use in person. As a result, this will add another subtest used exclusively on a computer, a tablet, an iPad, the like, etc. without needing additional materials. More assessment is being done virtually and this may make this subtest more viable for this format. In addition, virtual block test design 10 may remove the need for a norming disclaimer if the next version(s) are made and normed in this fashion.

In the specification and/or figures, typical embodiments of the disclosure have been disclosed. The present disclosure is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The foregoing description and drawings comprise illustrative embodiments. Having thus described exemplary embodiments, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments will come to mind to one skilled in the art to which this disclosure pertains having the benefit of the teachings presented in the foregoing descriptions and the associated drawings. Although specific terms may be employed herein, they are used in a generic and descriptive sense only and not for purposes of limitation. Accordingly, the present disclosure is not limited to the specific embodiments illustrated herein but is limited only by the following claims.

The invention claimed is:

1. A virtual block test system for psychology testing comprising:

a computer system having a processor, a memory, a client computer device including a user interface displayed on a client display screen and a client input device in communication with the user interface, a practitioner computer device having a practitioner display screen, and a client timer;

the memory is configured to store a plurality of virtual block tests via the processor;

the client display screen displays a specified virtual block test from the plurality of virtual block tests via the processor, wherein the specified virtual block test displayed on the client display screen including:

a sample solved block display including a plurality of solved blocks; and a plurality of virtual test blocks configured to be manipulated by the client via the client input device interacting with the user interface, the plurality of virtual test blocks include a same number of blocks as the plurality of solved blocks from the sample solved block display, and each of the plurality of virtual test blocks including a same pattern to mirror one of the plurality of solved blocks from the sample solved block display;

each of the plurality of virtual test blocks are a three-dimensional virtual cube configured to rotate and move;

the client input device is configured to manipulate the specified virtual block test displayed on the client display screen via the processor, the client input device is configured to rotate each of the plurality of virtual test blocks and to move each of the plurality of virtual test blocks, the client input device is selected from a group consisting of: a mouse; a keyboard; a touch screen for manipulation by a finger; a stylus pen; and combinations thereof, and wherein the computer system is configured to allow the client to take the specified virtual block test displayed on the client display screen by utilizing the mouse, the keyboard, the finger on the touch screen, the stylus pen, or the combinations thereof to manipulate the specified virtual block test;

the practitioner computer device is in communication with the client display screen over a network, wherein, the practitioner display screen is configured to mirror the client display screen on the practitioner computer device, and whereby, the practitioner computer device is configured to allow a practitioner to monitor the client taking the specified virtual block test via the practitioner display screen;

the practitioner computer device and the client computer device are paired via an interactive testing software program;

the client timer is configured to time the client while taking the specified virtual block test, wherein the practitioner display screen is configured to display an elapsed testing time from the client timer via the processor;

wherein, the computer system is configured to allow a client to take the specified virtual block test displayed on the client display screen via the user interface by utilizing the mouse, the keyboard, the finger on the touch screen, the stylus pen, or the combinations thereof to manipulate each of the plurality of virtual test blocks to orient and position each of the plurality of virtual test blocks to mirror the sample solved block display;

wherein the user interface includes:

a start button displayed on the client display screen, the start button is configured to activate the specified virtual block test, wherein, when the client is ready to begin the specified virtual block test, the client uses the client input device to press the start button on the display screen, whereby the client timer starts counting and displaying the elapsed testing time on the practitioner display screen until the specified virtual block test is completed;

the sample solved block display including the plurality of solved blocks displayed on the client display screen;

each of the plurality of virtual test blocks displayed on the display screen, wherein when the client clicks on one of the virtual test blocks with the client input device, the user interface takes movements from the client input device to manipulate and move each of the plurality of virtual test blocks; and an empty positioning base displayed on the display screen, the empty positioning base is sized and oriented to mirror a bottom of the sample solved block display, wherein, the specified virtual test block is completed via the user interface when the client manipulates and moves each of the plurality of virtual test blocks via the client input device to orient and position each of the plurality of virtual test blocks on the empty positioning base to mirror the sample solved block display.

2. The virtual block test system for psychology testing of claim 1, wherein the same number of blocks of the sample solved block display and the plurality of virtual test blocks is selected from a group consisting of: two blocks; four blocks; and nine blocks.

3. The virtual block test system for psychology testing of claim 1, wherein each of the plurality of virtual test blocks are configured to rotate and move between red faces, white faces, and red-white right triangle faces.

4. The virtual block test system for psychology testing of claim 1, wherein the specified virtual block test is manually selected from the plurality of virtual block tests or is randomly assigned from the plurality of virtual block tests via the processor.

5. The virtual block test system for psychology testing of claim 1, wherein the client computer device is selected from a group consisting of: a tablet; a personal computer; a desktop computer; a laptop; and a mobile device.

6. The virtual block test system for psychology testing of claim 1, wherein the practitioner computer device is selected from a group consisting of: a tablet; a personal computer; a desktop computer; a laptop; and a mobile device.

7. The virtual block test system for psychology testing according to claim 1 being designed and configured to update a Wechsler subtest to be conducted solely online with a virtual format.

8. A virtual block test system for psychology testing comprising:

a computer system having a processor, a memory, a client computer device with a client input device in communication with a user interface, a client timer, and a client display screen with the user interface displayed thereon, and a practitioner computer device with a practitioner display screen;

the client computer device and the practitioner computer device are selected from a group consisting of: a tablet; a personal computer; a desktop computer; a laptop; and a mobile device;

the memory is configured to store a plurality of virtual block tests via the processor;

the client display screen is configured to display a specified virtual block test from the plurality of virtual block tests via the processor, wherein the specified virtual block test is manually selected from the plurality of virtual block tests, or is randomly assigned from the plurality of virtual block tests via the processor;

the client input device is configured to manipulate the specified virtual block test through the user interface displayed on the client display screen via the processor, the specified virtual block test displayed on the client display screen including:

a sample solved block display including a plurality of solved blocks;

the plurality of virtual test blocks configured to be manipulated by a client via the client input device interacting with the user interface, the plurality of virtual test blocks include a same number of blocks as the plurality of solved blocks from the sample solved block display, and each of the plurality of virtual test blocks including a same pattern to mirror one of the plurality of solved blocks from the sample solved block display;

an empty positioning base, the empty positioning base is sized and oriented to mirror a bottom of the sample solved block display, wherein, the computer system is configured to allow the client to take the specified virtual block test displayed on the client display screen by utilizing the client input device to manipulate each of the plurality of virtual test blocks to orient and position each of the plurality of virtual test blocks on the empty positioning base to mirror the sample solved block display;

the client input device is configured to rotate each of the plurality of virtual test blocks and to move each of the plurality of virtual test blocks;

wherein the same number of blocks of the sample solved block display and the plurality of virtual test blocks is selected from a group consisting of: two blocks; four blocks; and nine blocks;

wherein each of the plurality of virtual test blocks are a three-dimensional virtual cube configured to rotate and move between red face, white faces, and red-white right triangle faces;

the client timer is configured to time the client while taking the specified virtual block test, the practitioner display screen is configured to display an elapsed testing time from the client timer via the processor, wherein the client display screen includes a start button, the start button is configured to activate the specified virtual block test;

wherein, when the client is ready to begin the specified virtual block test, the start button is configured to be pressed with the client input device, whereby the client timer starts counting and displaying the elapsed testing time until the specified virtual block test is completed;

the practitioner computer device is in communication with the client display screen over a network, the practitioner computer device and the client computer device are paired via an interactive testing software program;

wherein, the practitioner display screen is configured to mirror the client display screen on the practitioner computer device;

whereby, the practitioner computer device is configured to allow a practitioner to monitor the client taking the specified virtual block test via the practitioner display screen;

wherein, the computer system is configured to allow the client to take the specified virtual block test displayed on the client display screen via the user interface by utilizing the client input device to manipulate each of the plurality of virtual test blocks to orient and position each of the plurality of virtual test blocks to mirror the sample solved block display;

wherein the client input device is selected from a group consisting of: a mouse; a keyboard; a touch screen for manipulation by a finger; a stylus pen; and combinations thereof; and wherein the computer system is configured to allow the client to take the specified virtual block test displayed on the client display screen by utilizing the mouse, the keyboard, the finger on the touch screen, the stylus pen, or the combinations thereof to manipulate the specified virtual block test each of the plurality of virtual test blocks to orient and position each of the plurality of virtual test blocks to mirror the sample solved block display;

wherein the user interface includes:

the start button displayed on the client display screen, the start button is configured to activate the specified virtual block test, wherein, when the client is ready to begin the specified virtual block test, the client uses the client input device to press the start button on the display screen, whereby the client timer starts counting and displaying the elapsed testing time on the practitioner display screen until the specified virtual block test is completed;

the sample solved block display including the plurality of solved blocks displayed on the client display screen;

each of the plurality of virtual test blocks displayed on the display screen, wherein when the client clicks on one of the virtual test blocks with the client input device, the user interface takes movements from the client input device to manipulate and move each of the plurality of virtual test blocks; and the empty positioning base displayed on the display screen, the empty positioning base is sized and oriented to mirror a bottom of the sample solved block display, wherein, the specified virtual test block is completed via the user interface when the client manipulates and moves each of the plurality of virtual test blocks via the client input device to orient and position each of the plurality of virtual test blocks on the empty positioning base to mirror the sample solved block display.

9. A method of conducting a virtual block test for psychology comprising:

providing a computer system having a processor, a memory, a client computer device including a user interface displayed on a client display screen and a client input device in communication with the user interface, a practitioner computer device having a practitioner display screen, and a client timer, the memory is configured to store a plurality of virtual block tests via the processor, the client display screen is configured to display a specified virtual block test from the plurality of virtual block tests via the processor, the client input device is configured to manipulate the specified virtual block test via the user interface displayed on the client display screen via the processor, wherein the specified virtual block test displayed on the client display screen including:

a sample solved block display including a plurality of solved blocks; and a plurality of virtual test blocks configured to be manipulated by the client via the client input device interacting with the user interface, the plurality of virtual test blocks include a same number of blocks as the plurality of solved blocks from the sample solved block display, and each of the plurality of virtual test blocks including a same pattern to mirror one of the plurality of solved blocks from the sample solved block display;

each of the plurality of virtual test blocks are a three-dimensional virtual cube configured to rotate and move;

connecting the practitioner computer device with the client computer device over a network, whereby the practitioner computer device is in communication with the client computer device;

pairing the practitioner computer device and the client computer device via an interactive testing software program;

taking the specified virtual block test displayed on the client display screen by utilizing the client input device to manipulate each of the plurality of virtual test blocks on the user interface to orient and position each of the plurality of virtual test blocks to mirror the sample solved block displayed, where the client input device is configured to rotate each of the plurality of virtual test blocks via the user interface and to move each of the plurality of virtual test blocks via the user interface; wherein the user interface includes:

a start button displayed on the client display screen, the start button is configured to activate the specified virtual block test, wherein, when the client is ready to begin the specified virtual block test, the client uses the client input device to press the start button on the display screen, whereby the client timer starts counting and displaying the elapsed testing time on the practitioner display screen until the specified virtual block test is completed;

mirroring the client display screen from the client computer device on the practitioner display screen of the practitioner computer device, whereby, the practitioner computer device is configured to allow a practitioner to monitor the client taking the specified virtual block test via the practitioner display screen; and observing a client taking the specified virtual block test by watching the practitioner display screen with the client display screen mirrored thereon.

10. The method of claim 9, wherein the taking the specified virtual block test displayed on the client display screen by utilizing the client input device to manipulate the specified virtual block test on the client display screen including:

starting the client timer to begin the specified virtual block test;

viewing the sample solved block display including the plurality of solved blocks on the client display screen;

rotating each of the plurality of virtual test blocks via the client input device to mirror an orientation of each of the plurality of solved blocks;

moving each of the rotated plurality of virtual test blocks into position on an empty positioning base; and calculating the elapsed testing time to complete the test via the client timer.

* * * * *